United States Patent [19]

Hissong

[11] Patent Number: 5,456,250
[45] Date of Patent: Oct. 10, 1995

[54] LASER COMPATIBLE JET VENTILATION TUBE

[75] Inventor: James B. Hissong, Jacksonville, Fla.

[73] Assignee: Xomed-Treace, Inc., Jacksonville, Fla.

[21] Appl. No.: 963,164

[22] Filed: Oct. 19, 1992

[51] Int. Cl.$^6$ .................................................. A61M 16/00
[52] U.S. Cl. ............................. 128/207.14; 128/207.15; 128/200.26
[58] Field of Search ................... 128/200.26, 207.14, 128/207.15

[56] References Cited

U.S. PATENT DOCUMENTS

| | | | |
|---|---|---|---|
| 2,210,744 | 8/1940 | Winder | 128/207.15 |
| 4,378,796 | 4/1983 | Milhaud | 128/207.15 |
| 4,489,722 | 12/1984 | Ferraro et al. | 128/207.15 |
| 4,584,998 | 4/1986 | McGrail | 128/207.15 |
| 4,632,108 | 12/1986 | Geil | 128/207.15 |
| 4,825,858 | 5/1989 | Frankel | 128/207.15 |
| 4,834,087 | 5/1989 | Coleman et al. | 128/207.15 |
| 4,976,261 | 12/1990 | Gluck et al. | 128/207.15 |
| 5,019,057 | 5/1991 | Truckai | 604/282 |
| 5,065,757 | 11/1991 | Dragisic et al. | 128/207.15 |
| 5,139,019 | 8/1992 | Smith et al. | 128/207.15 |
| 5,193,533 | 3/1993 | Body et al. | 128/207.14 |

FOREIGN PATENT DOCUMENTS

| | | | |
|---|---|---|---|
| 0074809 | 3/1983 | European Pat. Off. | A61M 25/00 |
| 0420486 | 4/1991 | European Pat. Off. | A61M 29/02 |
| 0425361 | 5/1991 | European Pat. Off. | A61M 16/04 |

OTHER PUBLICATIONS

"New Endotracheal Tube For Laser Surgery of the Larynx", by Norton et al., Ann Otol 57:1975, pp. 544–557.

Primary Examiner—Edgar S. Burr
Assistant Examiner—Aaron J. Lewis
Attorney, Agent, or Firm—Gipple & Hale

[57] ABSTRACT

The jet ventilation tube includes a flexible conduit with a flexible monitoring line, a centering portion for centering the tube in a trachea and a flexible reinforcement member for the conduit. The conduit is formed of combustion resistant plastic material and the noncombustible reinforcement member is in the form of a straight or coiled wire. The straight wire reinforcement can be located outside the conduit, whereas the coiled wire reinforcement can be located inside or outside the conduit. The integrity of the conduit is maintained by the reinforcement member and helps prevent break-up of the conduit in the event of a laser strike. A centering portion of the jet tube can be reinforced with wire, formed as a segmented structure or as a spirally expanded extension of the reinforcing coil.

27 Claims, 4 Drawing Sheets

LASER COMPATIBLE JET VENTILATION TUBE

BACKGROUND OF THE INVENTION

This invention is directed to medical devices used during laser surgery and more particularly to an elongated endotracheal jet ventilation tube that, upon being impacted by a laser beam, will not support combustion and will remain substantially integral.

Jet ventilation is a method of enabling a patient to breathe during surgery by forcing anesthetic gases through a tube of relatively small diameter. Two known methods of jet ventilation include supraglottic jet ventilation and subglottic jet ventilation. Supraglottic jet ventilation is performed with a relatively small diameter tube attached to a laryngoscope. A distal end of the ventilation tube is sized to reach just above the vocal fold. Because the path to the vocal fold is relatively short and direct, the supraglottic jet ventilation tube need not be flexible and can be formed of a rigid biocompatible material such as stainless steel.

For subglottic jet ventilation, the tube must be of sufficient length to extend past the vocal fold, preferably into the trachea. Therefore, in subglottic jet ventilation it is advantageous for the tube to be easily flexed to conform to the curvature of a patient's airway. Since an airway conforming jet ventilation tube is needed for subglottic jet ventilation, the material of choice is usually flexible plastic such as polyvinylchloride (PVC) or silicone.

Unfortunately, PVC or silicone tubes can combust if struck by a laser beam. Thus there is general reluctance to use laser surgery with subglottic jet ventilation, especially if the surgical area is proximate to the ventilation tube. Consequently, the prospect of ventilation tube combustion in an operative field of anesthetic gases containing increased levels of oxygen or other combustion supportive gases has resulted in limited use of subglottic jet ventilation during laser surgery.

It is thus desirable to provide a subglottic jet ventilation tube that is sufficiently flexible to conform to a patient's airway and will not support combustion upon impact with a laser beam. Since a laser strike can also break apart a ventilation tube, it is also desirable to provide a subglottic jet ventilation tube that remains substantially integral upon impact by a laser beam.

OBJECTS AND SUMMARY OF THE INVENTION

Among the several objects of the invention may be noted the provision of a novel jet ventilation tube, a novel subglottic jet ventilation tube that is formed of a material which resists combustion upon impact by a laser beam, a novel subglottic jet ventilation tube that resists combustion and is flexible enough to conform to a patient's airway during installation of the tube, a novel subglottic jet ventilation tube that remains substantially integral upon impact by a laser beam, and a novel method of preventing laser induced combustion and breakup of a subglottic jet ventilation tube upon impact by a laser beam.

Other objects and features of the invention will be in part apparent and in part pointed out hereinafter.

In accordance with the invention, the laser compatible jet ventilation tube includes a flexible elongated conduit formed of a combustion resistant plastic material. A distal end of the conduit is provided with centering means for centering the delivery outlet in a trachea. The proximal end of the conduit is provided with a fitting that permits detachable connection of the conduit to anesthetic equipment. A noncombustible flexible reinforcement member is joined to a predetermined length of the conduit to enable the conduit to remain substantially integral as a result of impact to the jet tube by a laser beam.

In several embodiments of the invention the reinforcement member is in the form of an elongated wire encased in combustion resistant plastic material provided at an exterior surface of the conduit. The reinforcing wire can be located between the conduit and a gas monitoring line joined to the conduit to monitor gas levels during surgery.

In other embodiments of the invention the reinforcement member is in the form of a coil of noncombustible material such as metal. The reinforcing coil can be provided at the inside or outside of the conduit.

In instances where the coil is inside the conduit, the monitor line can also be inside the conduit. In instances where the coil is outside the conduit the monitor line can be inside or outside the coil.

The flexibility of the conduit and the reinforcing member, whether it is straight wire or coil, and the flexibility of the monitor line enable the jet tube to be flexed during installation to conform with the curvature of a patient's airway. When the distal end of the jet tube is directed into the trachea the centering means contact the side walls of the trachea to hold the jet tube in a stable position in the airway. Should a laser beam strike the jet tube, the components thereof will not support combustion and the reinforcing member will maintain the integrity of the jet tube. Thus the reinforcing member helps assure that the jet tube will not break into separate independent parts as a result of a laser strike because of the continuity of the reinforcing member along the vulnerable extent of the jet tube.

If desired, the distal end centering means can be similarly reinforced with noncombustible material such as metal similar to that used in the coil. In addition, the centering means can be formed as a segmented structure connected to the conduit at several places. Thus if a laser beam strikes the centering member and severs one or more but not all of the segmented portions, there is no separation of the conduit from the centering means. The centering member is thus maintained integral with the conduit despite a laser strike.

The method of preventing laser induced combustion and break up of a ventilation tube by a laser strike is to form the ventilation tube of a combustion resistant material that is sufficiently flexible to permit conformity of the tube to a patient's airway and to provide a combustion resistant monitoring line and centering means.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figures 1, 7:
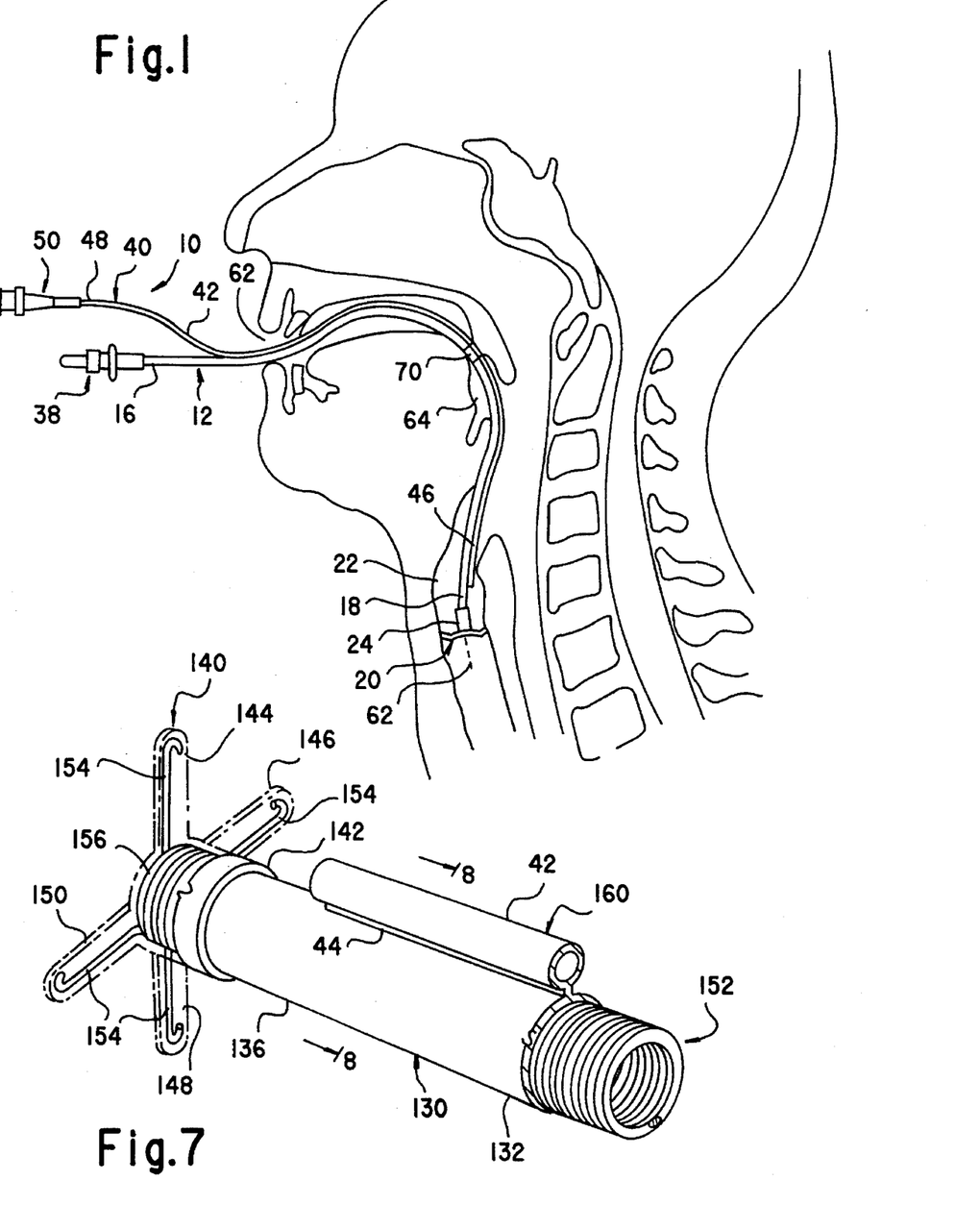
FIG. 1 is a simplified schematic view of a subglottic jet ventilation tube, incorporating one embodiment of the invention, in an installed position in a patient's airway.
FIG. 7 is a fragmentary perspective view of another embodiment of the invention.
Figures 2, 3, 4, 5, 6:
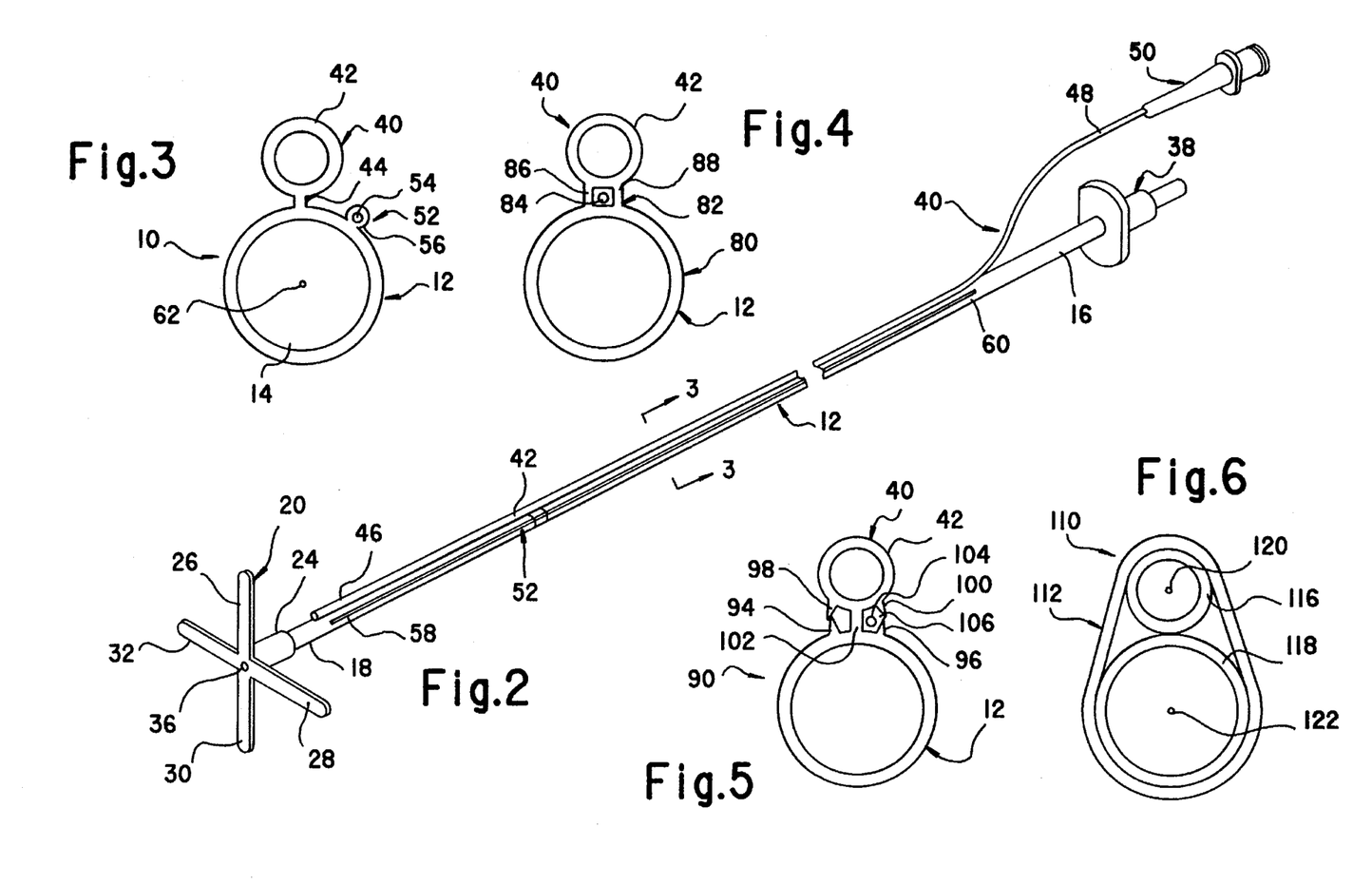
FIG. 2 is a simplified perspective view thereof.
FIG. 3 is a sectional view taken on the line 3—3 of FIG. 2.
FIGS. 4–6 are sectional views of other embodiments of the invention.

A laser compatible jet ventilation tube, or jet tube, incorporating one embodiment of the invention is generally indicated by the reference number 10 in FIGS. 1 and 2.

Referring to FIG. 2, the jet tube 10 comprises a flexible elongated conduit 12 of generally circular cross section with an inner passage 14 (FIG. 3), a proximal end portion 16 and a distal end portion 18. Preferably the conduit 12 is formed of a combustion resistant plastic material such as polytetrafluoroethylene, also sold under the trademark Teflon®.

The conduit 12, which can be formed by extrusion, by molding or by any other suitable known forming method, has a wall thickness in the range of 0.010 to 0.016 inches, and a diameter in the range of 0.080 to 0.100 inches. The overall length of the conduit 12 can be approximately 12 inches.

A centering member 20 is provided at the distal end portion 18 of the conduit 12 for centering the conduit 12 in a trachea 22 (FIG. 1). The centering member 20 is also preferably formed of polytetrafluoroethylene and includes a hub portion 24 that tightly receives the distal end portion 18 of the conduit 12. A Teflon® sleeve (not shown) can be shrunk-fitted around the hub 24 to overlap the distal end portion 18 of the conduit 12.

Centering fingers 26, 28, 30 and 32 radially project from the hub portion 24 and are spaced approximately 90° apart. The distance between opposite free ends of the fingers 26, 28, 30 and 32 is approximately 1¼ inches. An axial opening 36 (FIG. 2) is provided at the center of the centering fingers 26, 28, 30 and 32 in alignment with the inner passage 14 of the conduit 12. If desired, the centering member 20 can be after-molded onto the distal end 18 of the conduit 12.

A female luer fitting 38 of known construction is provided at the proximal end 16 of the conduit 12 for detachable securement to a known anesthesia supply apparatus (not shown).

A gas monitoring device 40 for monitoring the level of carbon dioxide at the trachea 22 includes a monitoring line 42 integrally formed with the conduit 12. The monitoring line 42 is joined to the conduit 12 by a bridging section 44 shown most clearly in FIG. 3. A distal end 46 of the monitoring line 42 is spaced a predetermined amount such as one inch from the centering fingers 26, 28, 30 and 32. A proximal end portion 48 of the monitoring line 42 includes a known female luer fitting 50 for detachable securement to a known gas analyzer section (not shown) of the monitoring device 40. The proximal end portion 48 is freely movable with respect to the conduit 12 to facilitate securement of the luer fitting 50 to the gas analyzer section.

A flexible elongated reinforcement member 52 (FIGS. 2 and 3) joined to the conduit 12 includes a wire 54, preferably formed of steel, encased in an elongated Teflon® jacket 56. The jacket 56 is preferably formed integrally with the conduit 12 and molded onto the wire 54.

The reinforcement member 52 has a distal end 58 (FIG. 2) at the centering fingers 26, 28, 30 and 32, and extends the full length of the conduit 12 to a proximal end 60.

In using the jet ventilation tube 10, the luer fitting 38 is connected to anesthesia equipment (not shown) and the luer fitting 50 is connected to the gas analyzer section (not shown) of the gas monitoring device 40. The centering fingers 26, 28, 30 and 32 of the centering member 20, which are flexible, can deflect in a proximal direction toward the axis 62 of the conduit 12 as shown in FIG. 1. The distal end portion 18 is directed through a patient's mouth 62, larynx 64, and into the trachea 22 along a curvilinear path that is characteristic of a typical airway.

A vocal cord indicator reference band 70 which can be a suitable known marking or coloring is provided on the conduit 12 a predetermined distance from the distal end portion 18 to facilitate installation of the distal end 18 to a desired depth in the trachea 22.

As will be seen from FIG. 1, the jet tube 10 is curved to conform to the airway of a patient and is structured to easily flex for convenient installation and removal.

The reinforcement member 52 is of a predetermined length to extend along a predetermined portion of the conduit 12 that is in the striking range of a laser beam used during laser surgery. If a laser beam strikes a portion of the conduit 12 in the airway path, the combustion resistant conduit material will not support combustion. However since a laser beam can sever or cause breakage of the conduit 12, the reinforcement member 52 operates to maintain a line of connection between any portions of the conduit that might otherwise separate or break because of a laser strike.

If the jet tube 10 is damaged because of a laser strike, the conduit 12 can be easily withdrawn from the airway and interchanged with a replacement jet tube 10. The centering fingers 26, 28, 30 and 32 of the centering member 20 are sufficiently flexible toward or away from the axis 62 of the conduit 12 to permit relatively easy installation and removal as desired.

Another embodiment of the jet ventilation tube is generally indicated by the reference number 80 in FIG. 4. A reinforcement member 82 of the jet ventilation tube 80 differs from the reinforcement member 52 by provision of a wire 84 similar to the wire 54 between two spaced junction walls 86 and 88 that join the monitoring line 42 to the conduit 12. The jet ventilation tube 80 is otherwise identical in structure and operation to the jet ventilation tube 10.

Another embodiment of the jet ventilation tube is generally indicated by the reference number 90 in FIG. 5. A reinforcement device 92 of the jet ventilation tube 90 includes a pair of axially elongated spaced resilient wing-like latch members 94 and 96 projecting radially from the conduit 12 for engagement with similar axially elongated spaced wing-like latch members 98 and 100 projecting radially from the monitoring line 42. A bridging section 102 similar to the bridging section 44 of the jet tube 10 in FIG.

3, joins the monitoring line 42 to the conduit 12. A reinforcement wire 104 is disposed in a space 106 between the bridging section 102 and the engagable latching members 98 and 100. The jet tube 90 is otherwise structurally and operationally similar to the jet tube 10.

A jet ventilation tube incorporating a further embodiment of the invention is generally indicated by the reference number 110 in FIG. 6. The jet tube 110 includes a conduit 112 formed of Teflon® which contains a gas monitoring line 116 provided on top of a main jet line 118 which is in the form of a wire coil. Thus the axis 120 of the monitoring line 116 and the axis 122 of the coil 118 are spaced from each other. The conduit 112 is preferably heat shrunk to tightly embrace the monitoring line 116 and the coil 118. The monitor line 116 is thus sandwiched between the wire coil 118 and the conduit 112.

The coil 118 extends substantially the full length of the conduit 112 and has a nominal inside diameter of approximately 0.080 to 0.100 inches. The coil 118 is preferably formed of stainless steel or copper wire, with a wire diameter of approximately 0.022 inches and approximately 45 coils per inch.

Figures 8, 9, 10, 11, 12:
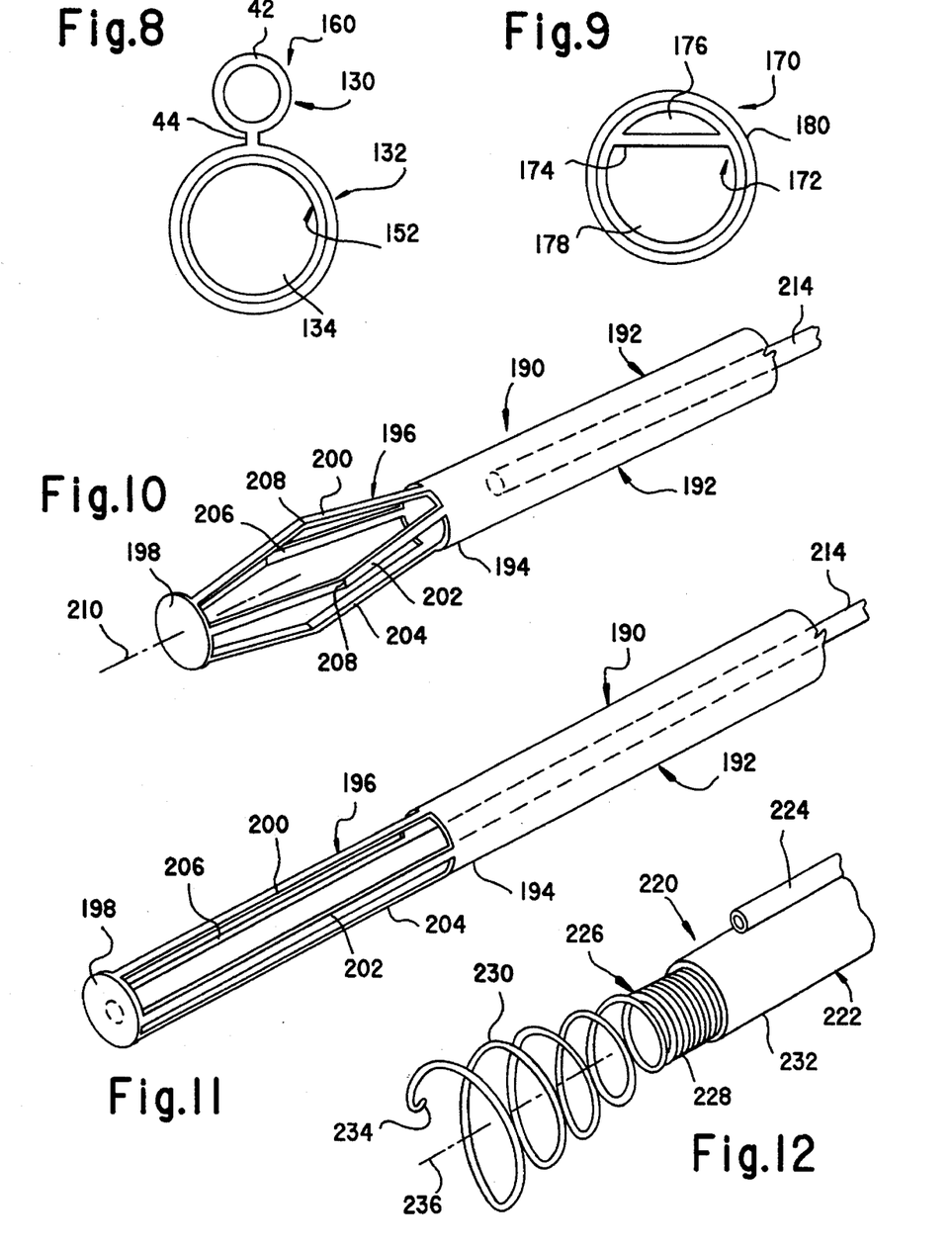
FIG. 8 is a sectional view taken on the line 7—7 of FIG. 8.
FIG. 9 is a sectional view of another embodiment of the invention.
FIG. 10 is a simplified fragmentary perspective view of still another embodiment of the invention.
FIG. 11 is a perspective view thereof with the distal portion in an extended position.
FIG. 12 is a fragmentary perspective view of another embodiment of the invention.

A distal end (not shown) of the coil 118 is spirally expanded in the manner shown at reference number 230 in FIG. 12 to form a centering member for centering the distal end of the conduit 112 in a trachea. Thus at the distal end of the jet tube 110 the monitoring line 116 is foreshortened and the conduit 112 surrounds the coil 118 in the manner shown at reference number 232 in FIG. 12.

The proximal end (not shown) of the conduit 112 can be capped in any suitable known manner, the cap being provided in a known manner with two known luer fittings (not shown). One fitting communicates with the monitor line 116 and the other fitting communicates with the main jet line 118. The fittings are adapted to connect to a known anesthesia apparatus (not shown) and a known gas monitoring device (not shown).

The coil 118 which is disposed along substantially the full length of the conduit 112 functions as the main anesthesia line member for the conduit 112. The coil 118 enables the jet tube 110 to resist breakage if struck by a laser beam since the coil is continuous within the conduit 112. The coil 118 thus maintains the integrity of the conduit 112 if a laser beam strikes the jet tube 110 during surgery.

A further embodiment of the jet ventilation tube is generally indicated by the reference number 130 in FIGS. 7 and 8. The jet tube 130 comprises a flexible elongated conduit 132 of generally circular cross section with an inner passage 134 (FIG. 8). The conduit 132 includes a proximal end portion (not shown) similar to the proximal end portion 16 of the jet tube 10. A distal end portion 136 (FIG. 7) of the conduit 132 is provided with a centering member 140 having a hub portion 142 and radially projecting centering fingers 144, 146, 148 and 150.

A reinforcement member 152 in the form of a coil is provided in the passageway 134 of the conduit 132 and extends from the proximal end (not shown) of the conduit 132 to the centering fingers 144, 146, 148 and 150. The reinforcement coil 152 does not have a spirally expanded distal end but is otherwise similar to the reinforcement coil 118 of the jet tube 110 (FIG. 6).

As most clearly shown in FIG. 7, J-shaped wires 154 are provided at each of the centering fingers 144, 146, 148 and 150 to reinforce the fingers, and are preferably joined in any suitable known manner to the distal end 156 of the coil 152. If desired, the plastic portion of the centering member 140 can be after-molded onto the J-shaped wires 154 and the distal end 136 of the conduit 132. Thus the centering fingers 144, 146, 148 and 150 encapsulate the J-shaped wires 154, and the hub portion 142 is molded onto the distal end 156 of the spring 152 as well as the distal end 136 of the conduit 132.

A gas monitoring device 160 similar to the gas monitoring device 40 is formed on the conduit 132 and both the conduit 132 and the monitoring line 42 can be molded onto the coil 152. The coil 152 thus maintains the integrity of the conduit 132 in the event of a laser strike during surgery. In addition, the J-shaped wires 154 maintain the integrity of the centering fingers 144, 146, 148 and 150 in the event of a laser strike. Thus the combination of the coil 152 and the J-shaped wires 154 help prevent significant parts of the jet tube 130 from breaking away from each other by preventing severance of the centering fingers 144–150 and preventing severance of the conduit 132 in the event of a laser strike. The jet ventilation tube 130 is installed and used in a manner similar to that previously described for the jet ventilation tube 10.

A further embodiment of the jet ventilation tube is generally indicated by the reference number 170 in FIG. 9. The jet tube 170 includes a conduit 172 of generally circular cross section. An elongated partition piece 174 is formed in the conduit 172 to divide the internal passageway into noncommunicable passage sections 176 and 178. The passage section 176 is used in a manner similar to that of the monitoring line 42 of the jet tube 10 and the passage section 178 functions in a manner similar to that of the passage 14 of the jet tube 10.

It should be noted that the monitoring passage 176 is foreshortened at the distal end (not shown) such that the gas passage section 178 extends beyond the monitoring line passage section 176 by approximately one inch. A proximal end (not shown) of the conduit 172 is capped and provided with separate connections to anesthesia apparatus and a gas monitoring device in a manner similar to that described for the jet tube 110 of FIG. 6.

A reinforcement coil 180 surrounds the conduit 172, extending to the distal end (not shown) of said conduit. The coil 180 can be spirally enlarged in the manner indicated at reference number 230 of FIG. 12 to form a centering member for centering the distal end of the conduit 172 in a trachea. The coil 180 can be slipped onto the conduit 172 or the conduit 172 can be molded in place inside the coil 180. In either case, the coil 180 maintains the integrity of the conduit 172 in the event of a laser strike to the conduit during surgery. The coil 180 is structured to permit the jet tube 170 to conform to a patient's airway for convenient installation and removal.

Still another embodiment of the jet tube is generally indicated by the reference number 190 in FIGS. 10 and 11. The jet tube 190 includes a conduit 192 generally circular in cross section. A centering member 196 is formed at a distal end 194 of the conduit 192 as an extension of the conduit 192. The centering member 196 is segmented and includes a terminal piece 198 and four radially spaced segments 200, 202, 204 and 206 of predetermined axial length and radial extent, extending from the terminal 198 to the distal end 194 of the conduit 192.

Each of the segments 200, 202, 204 and 206 include a preformed bend portion 208 (FIG. 10) which normally urges the segments 200, 202, 204 and 206 to bend in a direction radially away from the axis 210 of the conduit 192.

A reinforcement member which has been omitted for purposes of clarity, can be either the elongated wire reinforcement member 52 of the jet tube 10, the internal coil 152 of the jet tube 130, or the external coil 180 of the jet tube 170.

In using the jet tube 190, a flexible stylet 214 is inserted into the proximal end (not shown) of the conduit 192 to bear against the terminal piece 198 and straighten the segments 200, 202, 204 and 206 as shown in FIG. 11. The jet tube 190 and the stylet 214 are then installed in a patient's airway in a manner similar to that shown in FIG. 1. The flexibility of the conduit 192 and the stylet 214 permits conformity of the jet tube 190 with the patient's airway. When the distal end 194 of the jet tube 190 is located in the trachea, the stylet 214 is retracted from the proximal end (not shown) of the conduit 192 and removed to enable the segments 200, 202, 204 and 206 to assume their normally bent position and thus bear against the sides of the trachea. The conduit 192 is thus stabilized in the trachea.

Although not shown, the proximal end of the jet tube 190 is similar to that of the jet tube 10 and the luer fitting provided on the conduit 192 can be removed during installation and removal of the stylet 214 from the conduit.

The jet tube 190 is used in a manner similar to that previously described for other embodiments of this invention. Whichever reinforcement is used with the jet tube 190, the integrity of the conduit 192 is maintained as described for previous embodiments.

Although no reinforcement is provided at the segmented centering member 196, there is little likelihood that any portion thereof, even if broken due to a strike by a laser, can be separated from the jet tube. For example, if one of the segments 200–206 is severed or otherwise broken, the end portions remain connected to either the terminal piece 198 and the distal end 194 of the conduit 192. Furthermore, it is unlikely that all four segments 200, 202, 204 and 206 of the centering portion 196 would break simultaneously due to a laser strike because of the narrow scope of the laser beam.

Still another embodiment of the jet ventilation tube is generally indicated by the reference number 220 in FIG. 12. The jet ventilation tube 220 includes a conduit 222 similar to the conduit 12 with a monitoring line 224 similar to the monitoring line 42 of the jet tube 10. A reinforcement member 226 comprising a coil 228 similar to the coil 152 of the jet tube 130 is located inside the conduit 222. A distal end 230 of the coil 228 projects from the distal end 232 of the conduit 222 and is formed as a spirally expanded centering portion. A free end 234 of the centering portion 230 is bent toward the conduit axis 236 to avoid contact with other surfaces. The centering portion 230 is disposed in a trachea to center the jet tube 220 therein. The reinforcement coil 228 can be inserted in a preformed conduit 222 or the conduit 222 can be formed on the coil 228.

The proximal end (not shown) of the jet tube 220 is similar to the proximal end of the jet tube 10, and the jet tube 220 is used in the same fashion as the jet tube 10.

Figures 13, 14:
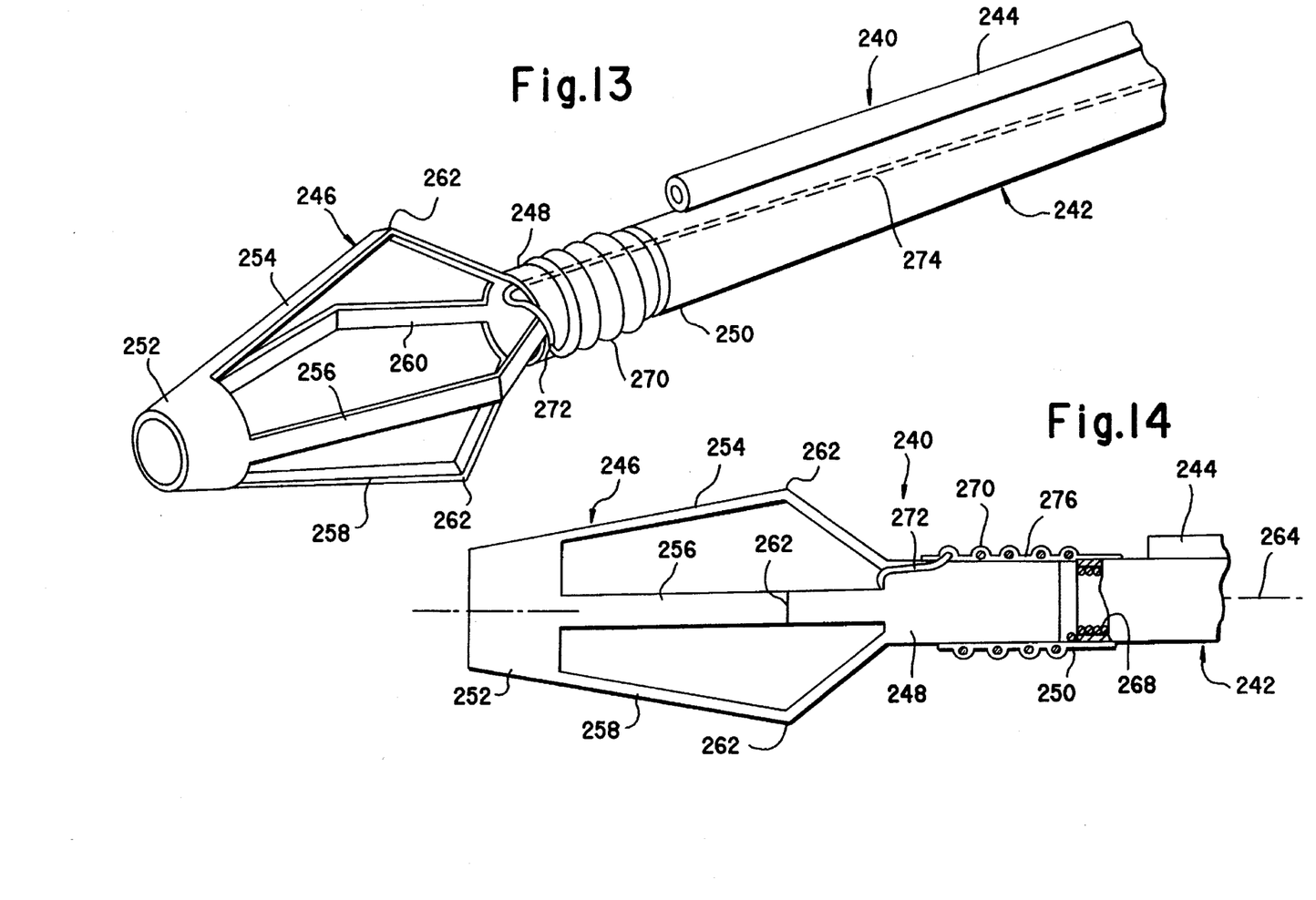
FIG. 13 is a perspective view of a further embodiment of the invention.
FIG. 14 is a fragmentary side view thereof, partly shown in section.

Still another embodiment of the jet ventilation tube is generally indicated by the reference number 240 in FIGS. 13 and 14. The jet tube 240 includes a conduit 242 having a monitoring line 244. The conduit 242 and the monitoring line 244 are similar to the corresponding structures 12 and 42 of the jet tube 10.

A centering member 246 includes a hub 248 engaged with a distal end 250 of the conduit 242. The centering member 246 further includes a terminal portion 252 in the form of a hollow frustum of a cone. The tapered contour of the terminal portion 252 of the centering member 246 facilitates insertion of the centering member 246 into a trachea. A plurality of radially spaced segments 254, 256, 258 and 260 of predetermined axial length and radial extent, extend from the terminal portion 252 to the hub 248. The segments include a preformed bend portion 262 to bias the segments 254, 256, 258 and 260 radially away from the axis 264 of the conduit 242 as shown in FIG. 14.

A reinforcement member 268 in the form of a coil is disposed within the conduit 242 and extends from a proximal end (not shown) to the distal end 250. An outer reinforcing necklace coil 270 encircles the hub 248 and a portion of the distal end 250 of the conduit 242. A strand 272 of the necklace coil 270 passes between the segments 254 and 256 for connection to the inner reinforcement coil 268. Alternatively, the strand 272 can extend axially within the conduit 242 toward the proximal end of the conduit, as indicated at 274 in FIG. 13. If desired, a Teflon® sleeve 276 can be shrunk-fitted around the external necklace coils 270.

Although not shown, the proximal end of the monitoring line 244 and the proximal end of the conduit 242 are similar to the corresponding structure in the jet tube 10.

In using the jet tube 240, the conduit 242 is conformed to the curvature of a patient's airway with the centering member 246 disposed in the trachea. During insertion of the centering member 246 in the trachea, the segments 254, 256, 258 and 260 are converged toward the axis 264 while passing through the larynx to the trachea. When the centering member 246 is located in the trachea, the segments 254, 256, 258 and 260 expand outwardly against the trachea wall to stabilize the distal end of the jet tube 240 in the trachea.

The jet tube 240 is used in a manner similar to that described for the jet tube 10. The integrity of the jet tube 240 is maintained by the inner reinforcement coil 268. Any breakage or separation of a segment 254–260 by a laser strike of any one segment will not cause separation of the centering member 246 from the conduit 242 since the remaining segments remain conjoined with the conduit 242 and the terminal end 252.

Some advantages of the present invention evident from the foregoing description include a jet ventilation tube that is combustion resistant if struck by a laser. The flexible combustion resistant reinforcement facilitates subglottic insertion of the ventilation tube and easy conformity of such tube to a patient's airway. The flexibility of the jet tube permits convenient installation and removal from a patient's airway and permits the favored subglottic use of a ventilation tube to provide a more efficient distribution of anesthesia to a patient's trachea than is otherwise obtainable with supraglottic jet ventilation tubes.

The combustion resistance of the jet ventilation tube and the capability of maintaining the integrity of the jet ventilation tube structure even when a laser strike occurs help assure safe and convenient use of a subglottic jet ventilation tube during laser surgery.

A further advantage is the assurance of stability of the jet ventilation tube in the trachea by use of a centering member having projecting fingers that can be reinforced with noncombustible wire, or a centering member having segments connected at opposite ends to the conduit and a terminal piece. An expanded spiral shaped centering piece formed of noncombustible material is another option to help assure stability and integrity of the centering portion of the jet ventilation tube in the trachea.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A subglottic jet ventilation device comprising,
   a) a flexible, elongated conduit formed of a combustion resistant plastic material having a proximal end portion and a distal end portion,
   b) a flexible, elongated nonwoven noncombustible metallic wire reinforcement member joined to said conduit to permit flexion of the conduit and extending continuously along said conduit from the proximal end portion of said conduit to enable said conduit to resist separation into separate pieces upon impact to said conduit by a laser beam, said metallic wire reinforcement member comprising a bendable straight wire portion that extends axially of said conduit from said proximal end portion of said conduit to said distal end portion of said conduit and flexes in conformity with said conduits, and
   c) centering means for centering the distal end of said conduit in a trachea.

2. The subglottic jet ventilation device as claimed in claim 1 wherein said wire is embedded in said conduit.

3. The subglottic jet ventilation device as claimed in claim 1 wherein said conduit has an outside surface and said wire is joined to said conduit at said outside surface.

4. The subglottic jet ventilation device as claimed in claim 1 further including an elongated monitor line joined to said conduit for monitoring gas levels during surgery.

5. The subglottic jet ventilation device as claimed in claim 4 wherein said monitor line is provided at the interior of said conduit.

6. The subglottic jet ventilation device as claimed in claim 4 wherein said conduit has an outside surface, said monitor line being joined to the outside surface of said conduit, and said wire being disposed between said monitor line and said conduit.

7. The subglottic jet ventilation device as claimed in claim 6 wherein said monitor line and said conduit include separable interengagable portions which form a closure between said monitoring line and said conduit, said wire being disposed in said closure.

8. The subglottic jet ventilation device as claimed in claim 6 wherein two spaced junction walls join said monitor line to said conduit and said wire is disposed in the space between said junction walls.

9. The subglottic jet ventilation device as claimed in claim 1 wherein said noncombustible metallic wire reinforcement member further includes a flexible, coil substantially concentric with said conduit and in contact with said conduit.

10. The subglottic jet ventilation device as claimed in claim 9 wherein said coil surrounds said conduit.

11. The subglottic jet ventilation device as claimed in claim 9 wherein said coil is inside said conduit.

12. The subglottic jet ventilation device as claimed in claim 9 wherein said coil has a distal end in the form of a spiral, at the distal end of said conduit.

13. The subglottic jet ventilation device as claimed in claim 9 wherein said centering means includes a terminal piece and a plurality of radially spaced segments of predetermined axial length and radial extent extending from said terminal piece to the distal end of said conduit.

14. The subglottic jet ventilation device as claimed in claim 13 wherein said centering means has four radially spaced segments.

15. The subglottic jet ventilation device as claimed in claim 13 wherein said terminal piece is a disk-shaped member and said segments join the periphery of said disk-shaped member.

16. The subglottic jet ventilation device as claimed in claim 13 wherein said terminal piece is annular.

17. The subglottic jet ventilation device as claimed in claim 16 wherein said annular terminal piece has a tapered periphery.

18. The subglottic jet ventilation device as claimed in claim 1 wherein said centering means includes a plurality of leg portions extending radially away from the axis of said conduit.

19. The subglottic jet ventilation device as claimed in claim 1 further including an elongated monitor line for monitoring gas levels during surgery and said reinforcement member further includes a coil, said monitor line and said coil being inside said conduit, the axis of said coil and the axis of said monitor line being axially spaced from each other such that said conduit embraces predetermined peripheral surface portions of said coil and said monitor line.

20. A subglottic jet ventilation tube comprising,
   a) a flexible elongated conduit formed of a combustion resistant plastic material having a proximal end portion and a distal end portion,
   b) a flexible, nonwoven, noncombustible metallic wire coil concentrically positioned around said conduit axis, and located inside an outer surface of said conduit to permit flexion of the conduit, said coil extending continuously along said conduit from the proximal end portion of said conduit to the distal end portion of said conduit to support said conduit and to enable said conduit to resist separation into separate pieces upon contact of said conduit by a laser beam, and
   c) centering means for centering the distal end of said conduit in a trachea.

21. The subglottic jet ventilation device as claimed in claim 20 wherein said centering means includes a terminal piece and a plurality of radially spaced segments of predetermined axial length and radial extent extending from said terminal piece to the distal end of said conduit, said segments being normally bent at a predetermined bend portion between said terminal piece and the distal end of said conduit such that the bent portions of said segments normally project radially away from the axis of said conduit.

22. The subglottic jet ventilation device as claimed in claim 21 further including an elongated monitoring line for monitoring gas levels during surgery, said monitoring line being joined to said conduit.

23. A method of preventing combustion and breakup of a subglottic jet ventilation tube upon impact by a laser comprising,
   a) forming the ventilation tube using a conduit of a combustion resistant flexible plastic material that can be conformed to a patient's airway during installation of the tube,
   b) providing the ventilation tube conduit with a flexible, nonwoven, noncombustible metallic wire reinforcement that extends continuously along the conduit from a proximal end portion of the conduit to a distal end portion of the conduit, the wire being selected such that it can be conformed to a patient's airway during installation of the tube,
   c) joining a gas monitoring tube to the conduit to monitor gas levels during surgery and forming the monitoring tube of a flexible combustion resistant material that can be conformed to a patient's airway during installation of the ventilation tube, and d) fixing the location of the conduit in a trachea by centering the distal end of the jet tube which is provided with a centering mechanism formed with a plurality of flexible arms by causing the flexible arms to engage against the inside wall of the trachea.

24. The method as claimed in claim 23 including forming the metallic wire reinforcement as a coil concentric with the conduit and inside the conduit such that the conduit is supported on the coil.

25. A subglottic jet ventilation device comprising, a) a flexible, elongated conduit formed of a combustion resistant plastic material having a proximal end portion and a distal end portion, b) a flexible, elongated noncombustible reinforcement member joined to said conduit for a predetermined length of said conduit to enable said conduit to resist separation into separate pieces upon impact to said predetermined length of conduit by a laser beam, said noncombustible reinforcement member comprising a flexible coil positioned substantially concentric with said conduit and in contact with said conduit, c) centering means for centering the distal end of said conduit in a trachea, said centering means including a terminal piece and a plurality of radially spaced segments of predetermined axial length and radial extent extending from said terminal piece and secured to the distal end of said conduit, and d) each of said segments being normally bent at a predetermined bend portion located between said terminal piece and the distal end of said conduit allowing the bent portions of said segments normally to project radially away from the axis of said conduit.

26. A subglottic jet ventilation device comprising, a) a flexible, elongated conduit formed of a combustion resistant plastic material having a proximal end portion and a distal end portion, b) a flexible, elongated noncombustible reinforcement member joined to said conduit for a predetermined length of said conduit to enable said conduit to resist separation into separate pieces upon impact to said predetermined length of conduit by a laser beam, and c) centering means for centering the distal end of said conduit in a trachea, and wherein d) said centering means includes a plurality of leg portions extending radially away from the axis of said conduit, and wherein, e) each of said leg portions has a wire reinforcement.

27. The subglottic jet ventilation device as claimed in claim 26 wherein said reinforcement member includes a noncombustible coil concentric with said conduit and in contact with said conduit and connected to said wire reinforcements.

* * * * *